(12) United States Patent
Olivo et al.

(10) Patent No.: US 9,913,767 B2
(45) Date of Patent: Mar. 13, 2018

(54) PORTABLE, INFLATABLE MATTRESS FOR LIFTING AND TRANSPORTING CORPSES

(71) Applicant: G2C Technologies, Austin, TX (US)

(72) Inventors: Inger Olivo, Austin, TX (US); John Peyton, Austin, TX (US)

(73) Assignee: G2C Technologies, Austin, TX (US)

( * ) Notice: Subject to any disclaimer, the term of this patent is extended or adjusted under 35 U.S.C. 154(b) by 193 days.

(21) Appl. No.: 14/788,084

(22) Filed: Jun. 30, 2015

(65) Prior Publication Data

US 2017/0000667 A1    Jan. 5, 2017

(51) Int. Cl.

| | |
|---|---|
| *A61G 1/013* | (2006.01) |
| *A61G 7/10* | (2006.01) |
| *A47C 27/08* | (2006.01) |
| *A61B 6/04* | (2006.01) |
| *A61G 1/044* | (2006.01) |

(Continued)

(52) U.S. Cl.
CPC .............. *A61G 1/013* (2013.01); *A47C 27/08* (2013.01); *A61B 6/0485* (2013.01); *A61G 1/003* (2013.01); *A61G 1/044* (2013.01); *A61G 7/103* (2013.01); *A61G 7/1021* (2013.01); *A61G 1/048* (2013.01); *A61G 2200/32* (2013.01)

(58) Field of Classification Search
CPC ....... A47C 27/001; A47C 27/10; A47C 27/08; A47C 27/081; A47C 27/085; A61G 1/013; A61G 1/044; A61G 7/1021; A61G 7/1026; A61G 7/1028; A61G 7/05761; A61G 7/05769; A61G 7/05776; A61G 2200/32; A61G 7/103; A61G 1/003; A61G 1/048; A61B 6/0485

See application file for complete search history.

(56) References Cited

U.S. PATENT DOCUMENTS

| | | | | |
|---|---|---|---|---|
| 1,324,687 | A | * 12/1919 | Newby | ................. B63H 16/14 440/32 |
| 3,711,879 | A | *  1/1973 | Siefert | ..................... B63C 9/32 114/43 |

(Continued)

OTHER PUBLICATIONS

Inger Olivo & John Peyton, Picture of preliminary prototype during developmental stage of inflatable mattress, 1 page, picture provided as Display Only on clipboard (no additional copies of picture were taken or provided), National Funeral Directors Association conference, Jun. 12-13, 2013.

*Primary Examiner* — Robert G Santos
*Assistant Examiner* — David R Hare
(74) *Attorney, Agent, or Firm* — Meyertons, Hood, Kivlin, Kowert & Goetzel, P.C.

(57) ABSTRACT

An inflatable mattress is placed in a deflated state at a location a human corpse departed from life. The inflatable mattress may include two elongated chambers and one rectangular mattress chamber that supports the human corpse. The inflatable mattress may include one or more devices for coupling the human corpse to a top surface of the inflatable mattress. An inflation device coupled to the inflatable mattress is used to inflate the inflatable mattress to a selected height in less than about 2 minutes with the human corpse coupled to the inflatable mattress. The inflatable mattress is movable, with the human corpse coupled to the inflatable mattress, from the location the human corpse departed from life to a secondary location.

19 Claims, 5 Drawing Sheets

(51) Int. Cl.
*A61G 1/003* (2006.01)
*A61G 1/048* (2006.01)

(56) References Cited

U.S. PATENT DOCUMENTS

| | | | | |
|---|---|---|---|---|
| 3,729,002 A * | 4/1973 | Miller | ............ | B63C 11/325 128/205.26 |
| 3,775,782 A * | 12/1973 | Rice | ............ | A61G 1/00 128/DIG. 20 |
| 3,887,953 A * | 6/1975 | Eisenhauer | ............ | B63C 9/04 244/137.2 |
| 4,301,791 A * | 11/1981 | Franco, III | ............ | A61F 5/055 128/870 |
| 4,347,635 A * | 9/1982 | Eisenhauer | ............ | A47C 1/143 280/18 |
| 4,466,145 A * | 8/1984 | Jones | ............ | A61G 1/00 441/40 |
| 4,717,362 A * | 1/1988 | Kraft | ............ | B63C 9/02 280/18 |
| 4,736,474 A * | 4/1988 | Moran | ............ | A61G 1/007 5/627 |
| 5,283,916 A * | 2/1994 | Haro | ............ | A61G 1/00 244/118.5 |
| 5,421,757 A * | 6/1995 | Basiliere | ............ | B63C 9/04 441/128 |
| 6,053,534 A * | 4/2000 | Timmerman | ............ | A62B 1/02 280/17 |
| 6,073,291 A | 6/2000 | Davis | | |
| 6,085,372 A * | 7/2000 | James | ............ | A61G 7/001 5/713 |
| 6,641,446 B1 * | 11/2003 | Bentley | ............ | B62B 13/06 280/19 |
| 6,701,544 B2 | 3/2004 | Heimbrock | | |
| 6,775,868 B1 * | 8/2004 | Mileti | ............ | A47C 27/001 5/710 |
| 6,964,073 B1 * | 11/2005 | Curry | ............ | A61G 1/00 128/870 |
| 7,114,204 B2 | 10/2006 | Patrick | | |
| 7,406,723 B2 * | 8/2008 | Davis | ............ | A61G 7/05769 5/706 |
| 7,666,046 B2 | 2/2010 | Larochelle | ............ | B63C 9/04 441/40 |
| 7,735,164 B1 | 6/2010 | Patrick | | |
| 8,234,727 B2 | 8/2012 | Schreiber et al. | | |
| 8,328,592 B2 * | 12/2012 | Cynamon | ............ | A61G 1/01 441/40 |
| 9,259,368 B2 * | 2/2016 | Jensen | ............ | A61G 1/013 |
| 2002/0144343 A1 * | 10/2002 | Kuiper | ............ | A61G 7/001 5/81.1 R |
| 2002/0166168 A1 | 11/2002 | Weedling et al. | | |
| 2003/0106155 A1 * | 6/2003 | Arai | ............ | A61G 1/00 5/627 |
| 2008/0289102 A1 | 11/2008 | Davis | | |
| 2012/0284923 A1 * | 11/2012 | Jensen | ............ | A61G 1/04 5/627 |
| 2014/0232156 A1 * | 8/2014 | Mills | ............ | A61G 5/14 297/338 |
| 2015/0283007 A1 * | 10/2015 | Carlson | ............ | A61G 1/013 5/627 |

* cited by examiner

PORTABLE, INFLATABLE MATTRESS FOR LIFTING AND TRANSPORTING CORPSES

BACKGROUND

1. Field of the Invention

The present invention relates to an inflatable lift and transport apparatus. More particularly, the invention relates to an inflatable and portable apparatus for lifting and transporting corpses.

2. Description of Related Art

Humans often may pass away at locations that may have difficult or cumbersome access for accessing the corpse. For example, the corpse may be located at a home or other location that is not generally equipped or designed for easy access and movement of a corpse. In such situations, the corpses can be difficult to remove from the location.

The typical method used for removing corpses from such locations includes lifting and placing the body on some type of surface (e.g., a cot or board such as a "highway cot") or putting the body in a bag with no support. The corpse may then be moved to a gurney for removal from the location. However, the distance between the corpse's location and the gurney may be significant and/or involve difficult maneuvers such as, but not limited to, going up/down stairs, around tight corners, and through doorways. Lifting and moving the corpse on a cot may be difficult and can cause injury to personnel as the corpse may have to be maneuvered into a variety positions (e.g., placed fully upright) to move the corpse through various locations (e.g., doorways or corners). Additionally, if the corpse is fairly heavy (e.g., above about 250 pounds), it may be difficult or dangerous to continually try to change a position of the corpse as well as being physically taxing.

In certain cases, additional support for lifting and/or moving the corpse may be desirable. The location of the corpse and/or the distance the corpse has to travel before being placed on the gurney may, however, not allow additional support to be easily provided. Thus, there is a need for devices and methods that allow personnel to more easily access and transport corpses at locations that are not generally equipped or designed for easy access and movement of the corpse.

SUMMARY

In certain embodiments, an inflatable mattress can be placed in a deflated state at a location a human corpse departed from life. In some embodiments, the inflatable mattress includes two elongated chambers and one rectangular mattress chamber that supports the human corpse. The inflatable mattress may include one or more devices for coupling the human corpse to a top surface of the inflatable mattress. An inflation device coupled to the inflatable mattress may be used to inflate the inflatable mattress to a selected height in less than about 2 minutes with the human corpse coupled to the inflatable mattress. The inflatable mattress is movable, with the human corpse coupled to the inflatable mattress, from the location the human corpse departed from life to a secondary location.

In certain embodiments, a method for lifting and transporting a human corpse includes moving the human corpse onto an inflatable mattress that is in a deflated state and securing the human corpse to at least part of a top surface of the inflatable mattress. The inflatable mattress may be at least partially inflated with compressed gas provided into the inflatable mattress to raise the human corpse located on the surface of the mattress a selected height, in less than about 2 minutes. The raised human corpse may be transferred from the inflated mattress to another location.

BRIEF DESCRIPTION OF THE DRAWINGS

Features and advantages of the methods and apparatus of the present invention will be more fully appreciated by reference to the following detailed description of presently preferred but nonetheless illustrative embodiments in accordance with the present invention when taken in conjunction with the accompanying drawings in which.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but to the contrary, the intention is to cover all modifications, equivalents and alternatives falling within the spirit and scope of the present invention as defined by the appended claims.

DETAILED DESCRIPTION OF EMBODIMENTS

In the context of this patent, the term "coupled" means either a direct connection or an indirect connection (e.g., one or more intervening connections) between one or more objects or components. The phrase "directly connected" means a direct connection between objects or components such that the objects or components are connected directly to each other so that the objects or components operate in a "point of use" manner.

Figures 1, 2:
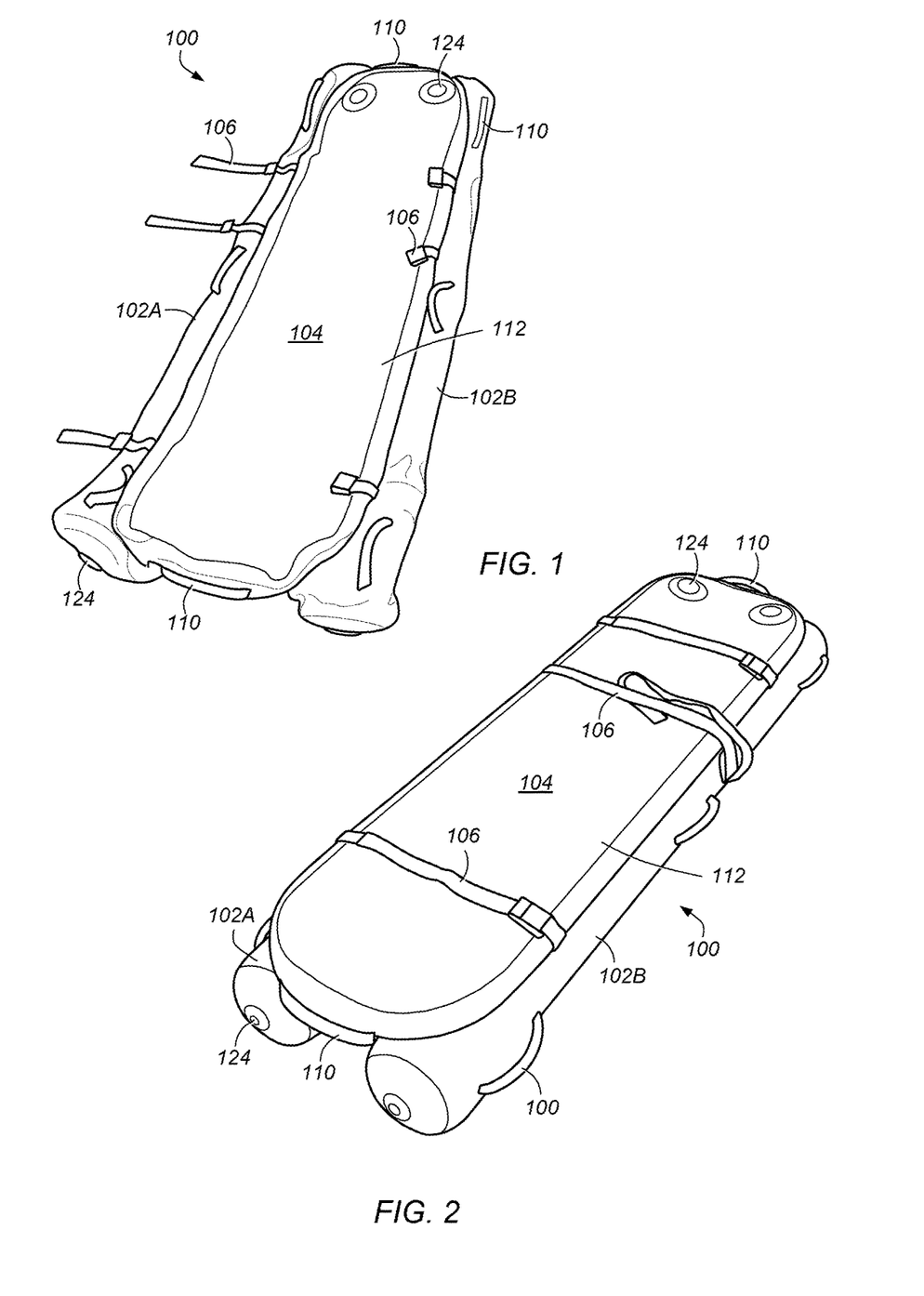
FIG. 1 depicts a top perspective view of an embodiment of an inflatable mattress for lifting and transporting a human corpse in a deflated state.
FIG. 2 depicts a top perspective view of an embodiment of an inflatable mattress for lifting and transporting a human corpse in an inflated state.

FIG. 1 depicts a top perspective view of an embodiment of an inflatable mattress for lifting and transporting a human corpse in a deflated state. FIG. 2 depicts a top perspective view of an embodiment of an inflatable mattress for lifting and transporting a human corpse in an inflated state. In certain embodiments, mattress 100 includes two elongated chambers 102A, 102B attached to rectangular mattress chamber 104. Elongated chambers 102A, 102B may be attached to rectangular mattress chamber 104 along the length of the rectangular mattress chamber.

Chambers 102A, 102B and chamber 104 may be made from strong, pliant materials that can be inflated/deflated repeatedly. For example, chambers 102A, 102B and chamber 104 may be made from neoprene or another similar washable polymer material. In the deflated stated shown in FIG. 1, the materials for chambers 102A, 102B and chamber 104 allow mattress 100 to be folded or rolled into a compact shape. The rolled, compact shape may allow mattress 100 to be more easily transported and/or stored.

In the inflated state, shown in FIG. 2, chambers 102A, 102B may form elongated shapes such as tubulars or cylinders. Chambers 102A, 102B may, for example, resemble pontoons when inflated. Chamber 104 may form a rectangular table shape when inflated. When inflated, chamber 104 may form a shape substantially similar to a thin mattress for supporting a human body. In certain embodiments, chamber 104 has a firm upper surface when inflated to support the human body. Additionally, chambers 102A, 102B may be firm and strong when inflated to provide support for chamber 104 and the corpse or human body.

Figure 3:
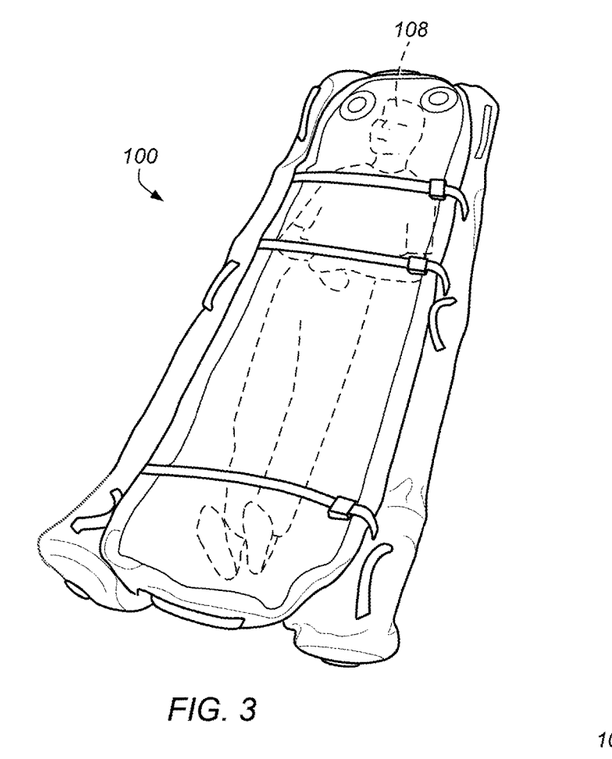
FIG. 3 depicts a top perspective view of an embodiment of a corpse secured to an inflatable mattress (in a deflated state) with straps.

In certain embodiments, as shown in FIGS. 1 and 2, mattress 100 includes one or more straps 106 attached to chamber 104. Straps 106 may be used to secure a corpse or human body to chamber 104 and mattress 100. FIG. 3 depicts a top perspective view of an embodiment of corpse 108 secured to mattress 100 (in a deflated state) with straps 106. Straps 106 may be, for example, adjustable and/or tensioned straps that can securely hold a body on mattress 100.

In certain embodiments, as shown in FIGS. 1-3, mattress 100 includes one or more handles 110 attached to chambers 102A, 102B and chamber 104. Handles 110 may be used to lift or maneuver mattress 100 when in either a deflated or inflated state. Handles 110 may be positioned at multiple locations around the perimeter of chambers 102A, 102B and chamber 104 to allow one or more personnel to easily grasp and maneuver mattress 100. Handles 110 may be positioned closer to an upper surface of mattress 100. Positioning handles 110 closer to the top of mattress 100 allows easier access to the handles.

In certain embodiments, the upper surface of rectangular mattress chamber 104 includes sliding material surface 112. Sliding material surface 112 may include, for example, a cloth, felt, fiber surface, or other textured material. In some embodiments, sliding material surface 112 includes washable material. Sliding material surface 112 may provide a more suitable surface for sliding or moving the corpse on/off mattress 100. In some embodiments, sliding material surface 112 has a coefficient of friction that is low enough to allow a corpse (e.g., a human body) to easily slide onto mattress 100. The coefficient of friction, however, is also high enough to inhibit the corpse from easily sliding off mattress 100 when the mattress and the attached corpse are moved over and/or around objects such as furniture or stairs.

Figure 4:
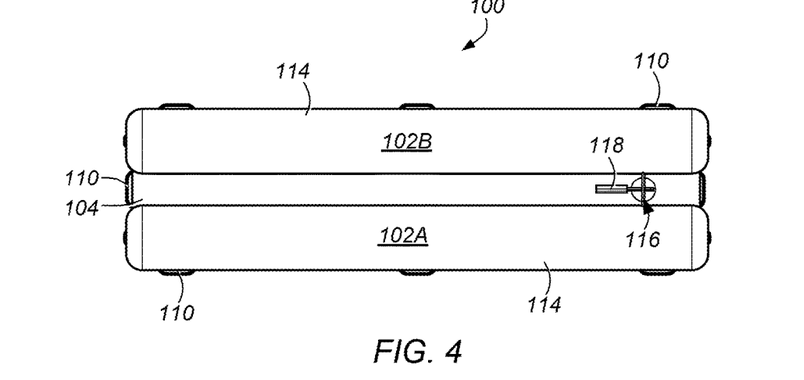
FIG. 4 depicts a bottom perspective view of an embodiment of an inflatable mattress in an inflated state.

FIG. 4 depicts a bottom perspective view of an embodiment of mattress 100 in an inflated state. In certain embodiments, the bottom surface of chambers 102A, 102B include sliding material surfaces 114. Sliding material surfaces 114 may include, for example, cloth, felt, or fiber surfaces. In some embodiments, sliding material surfaces 114 include washable material. Sliding material surfaces 114 may provide sliding or gliding surfaces for maneuvering mattress 100 on, over, and around various surfaces (e.g., up/down stairs, around wall corners, over furniture, etc.). In some embodiments, sliding material surfaces 114 have has coefficients of friction that are low enough to allow mattress 100 to slide on a number of different surfaces (e.g., carpeting, wood, grass, etc.). The coefficients of friction, however, are also high enough to inhibit mattress 100 from sliding too easily such that the mattress will slide uncontrollably on certain surfaces (e.g., the mattress has some friction when sliding on a hardwood floor).

Figure 5:
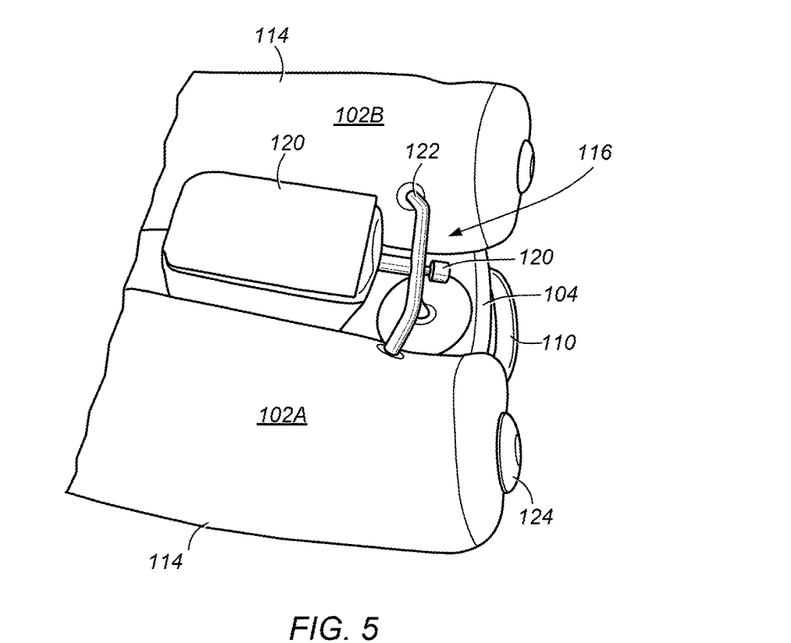
FIG. 5 depicts an enlarged perspective view of an embodiment of an inflation device attached to an inflatable mattress.

In certain embodiments, as shown in FIG. 4, inflation device 116 is attached to mattress 100. Inflation device 116 may, for example, be attached to a lower surface of chamber 104 between chambers 102A, 102B. FIG. 5 depicts an enlarged perspective view of an embodiment of inflation device 116 attached to mattress 100. Inflation device 116 may be positioned between chambers 102A, 102B and near chamber 104. Positioning inflation device 116 between chambers 102A, 102B may provide protection for the inflation device from being inadvertently struck or damaged. Positioning inflation device 116 between chambers 102A, 102B may also allow the inflation device to be protected and secured when mattress 100 is rolled or folded for storage or transport. In some embodiments, inflation device 116 is covered to further protect the inflation device. For example, inflation device 116 may be positioned in a pouch attached to chamber 104. The pouch may further protect and secure inflation device 116.

In certain embodiments, inflation device 116 includes compressed gas cylinder 118, regulator valve 120, and gas lines 122. Gas cylinder 118 may be a standard compressed gas cylinder. For example, gas cylinder 118 may be a compressed carbon dioxide gas cylinder. Gas cylinder 118 may be of sufficient size to provide gas for more than one inflation of mattress 100 while being sized to be positioned between chambers 102A, 102B. For example, gas cylinder 118 may be a 20 ounce tank of compressed carbon dioxide.

Gas cylinder 118 may be coupled to, or include, regulator 120. Regulator valve 120 may be a user operated valve to control the flow of gas into chambers 102A, 102B and chamber 104. Gas may be provided to chambers 102A, 102B and chamber 104 through gas lines 122. Regulator valve 120 may control (regulate) the flow of compressed gas into chambers 102A, 102B and 104 when the valve is opened. The flow of compressed gas may be controlled to control or regulate the inflation time for chambers 102A, 102B and chamber 104. Thus, when regulator 120 is opened, compressed gas controllably flows into chambers 102A, 102B and chamber 104 and fills the chambers in a desired amount of time.

In certain embodiments, chambers 102A, 102B and chamber 104 include pressure relief valves 124, as shown in FIGS. 1-3. Pressure relief valves 124 may be used to deflate chambers 102A, 102B and chamber 104 after use. Pressure relief valves 124 may controllably release gas from chambers 102A, 102B and chamber 104 and deflate the chambers in a desired amount of time. Pressure relief valves 124 may be operated individually to allow each chamber to be deflated individually as needed and/or desired.

In certain embodiments, mattress 100 is used to assist in lifting and transporting a human corpse. For example, mattress 100 may be transported to a location the human corpse departed from life (e.g., the location of death). Mattress 100 may be transported to the location in a deflated state. In some embodiments, mattress 100 is transported to the location in a rolled-up state (e.g., the mattress is rolled into a compact shape and transported to the location). In some embodiments, mattress 100 is transported in the rolled-up state in a carry bag (e.g., a hand carried bag).

Figure 6:
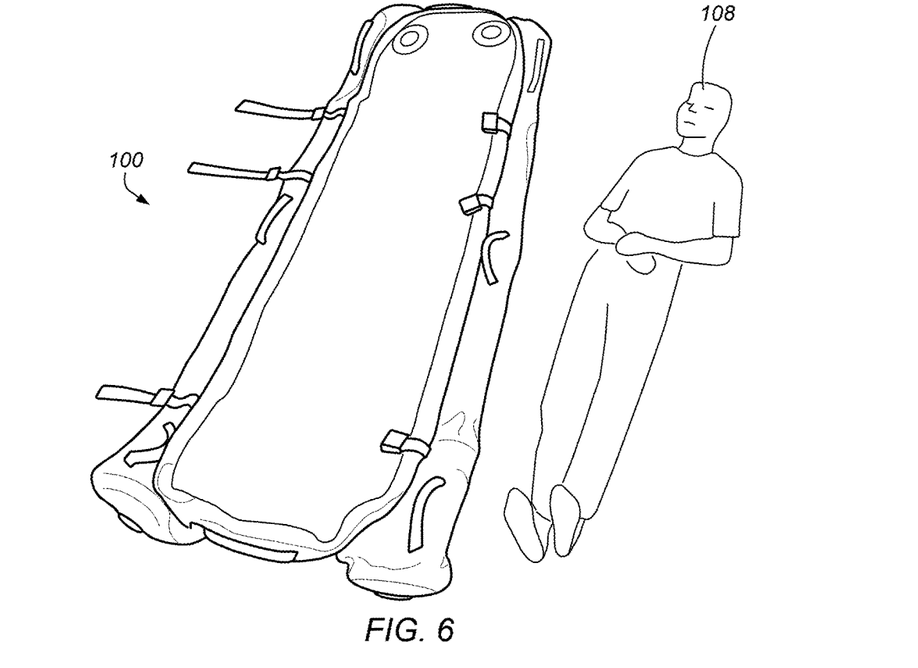
FIG. 6 depicts a representation of an inflatable mattress positioned adjacent to a corpse at the location of death.

In certain embodiments, after mattress 100 is placed adjacent to corpse 108 (e.g., human corpse) at the location of death, the mattress is unrolled (if in rolled-up state) and positioned next to corpse 108, as shown in FIG. 6. After mattress 100 is positioned next to corpse 108, the corpse may be moved onto the mattress, which is in a deflated state, as shown in FIG. 3. In some embodiments, corpse 108 is moved onto mattress 100 by at least partially lifting the corpse and sliding the mattress underneath the corpse (e.g., log rolling the corpse and placing the mattress under the corpse). In some embodiments, an additional device is used to assist in placing corpse 108 on mattress 100. For example, a thin board, such as a Smooth Mover or other polyethylene board, may be slid under corpse 108 and used to assist in lifting the corpse onto mattress 108. The thin board may be left under corpse 108 and positioned on mattress 100 along with the corpse.

Figures 7, 8:
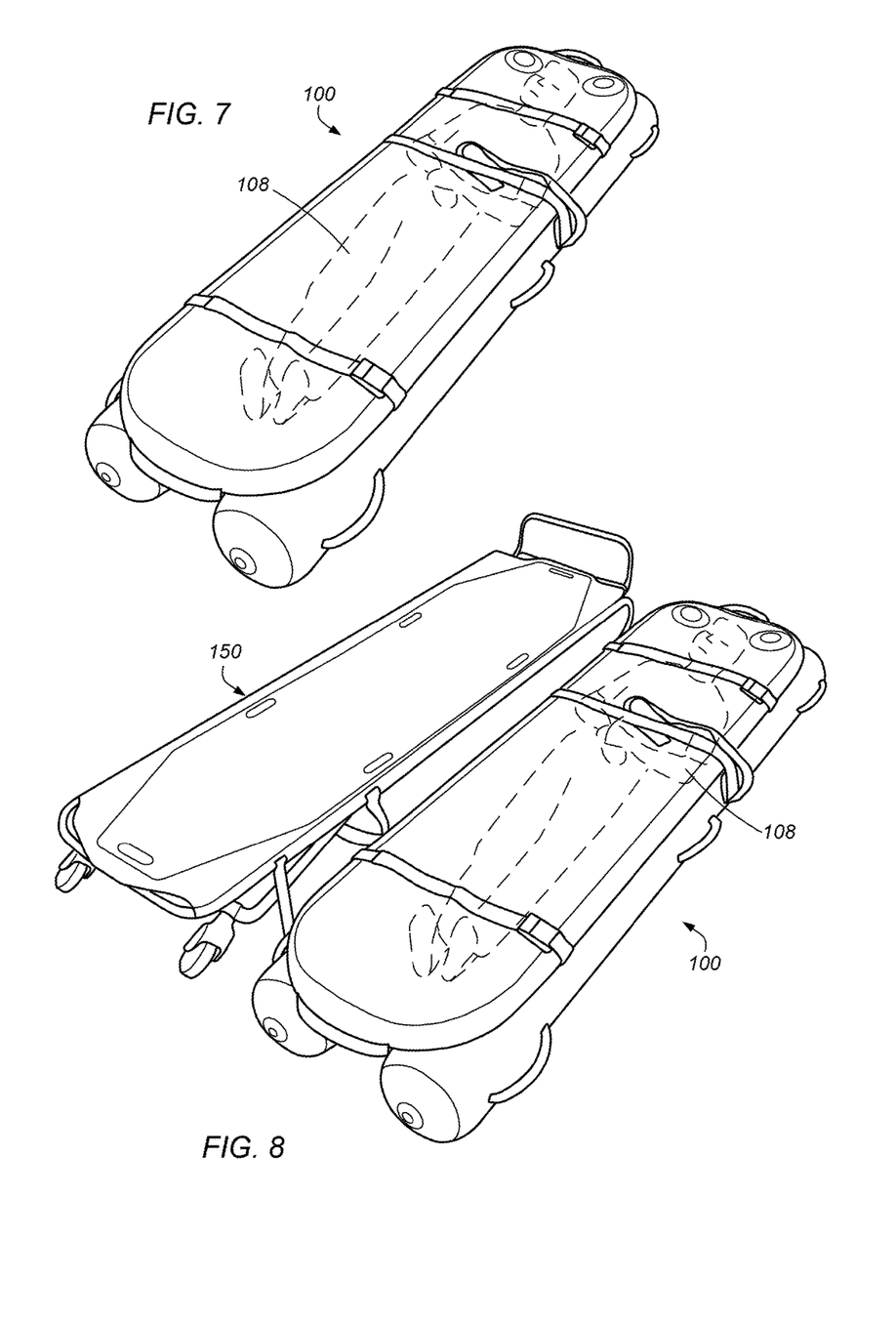
FIG. 7 depicts a representation of an embodiment of a corpse on an inflatable mattress in an inflated state.
FIG. 8 depicts a representation of an embodiment of a corpse on an inflatable mattress, in the inflated state, positioned next to a gurney.

After corpse 108 is positioned on mattress 100, the corpse may be secured to the mattress using straps 106, as shown in FIG. 3. Once corpse 108 is secured to mattress 100, the mattress may be inflated using, for example, inflation device 116 (shown in FIGS. 4 and 5). FIG. 7 depicts a representation of an embodiment of corpse 108 on mattress 100 in an inflated state. Mattress 100 is inflated by providing compressed gas from inflation device 116 into chambers 102A, 102B and chamber 104. Inflation of the chambers inflates mattress 100 to an inflated state.

In the inflated state, chambers 102A, 102B provide support to mattress chamber 104 (e.g., the "mattress" of mattress 100). Because chambers 102A, 102B are tubular "pontoons" and chamber 104 is a thin, relatively flat chamber, less gas to inflate mattress 100 than if an entire mattress with the same cross-section as chambers 102A, 102B and chamber 104 was inflated (e.g., mattress 100 with chambers 102A, 102B and chamber 104 uses less gas to inflate than would a single chamber mattress having the same outer dimensions as mattress 100).

In certain embodiments, as shown in FIG. 7, chambers 102A, 102B have at least some portion that extends beyond the longitudinal edges of chamber 104, in the inflated state. For example, about ½ of chambers 102A, 102B may extend beyond the longitudinal edges of chamber 104. Chambers 102A, 102B may provide additional support and stability in mattress 100 by extending beyond the longitudinal edges of chamber 104. For example, chambers 102A, 102B have portions under chamber 104 that provide support to chamber 104 while the extension of the chambers beyond the edge of chamber 104 provides a wider base that improves stability of mattress 100. Additionally, the use of two elongated chambers 102A, 102B provides more stability than if only one chamber is used to support mattress chamber 104.

In certain embodiments, mattress 100 is inflated to a selected height. In some embodiments, the selected height is a height substantially similar to a lowered height of a gurney or mortuary cot. For example, the selected height may be about 12". In some embodiments, the selected height is between about 12" and about 18".

In certain embodiments, mattress 100 is inflated to the selected height in a desired amount of time. For example, in some embodiments, mattress 100 is inflated to the selected height in less than about 2 minutes. In some embodiments, mattress 100 is inflated to the selected height in less than about 90 seconds (1 minute, 30 seconds). The desired time for inflation of mattress may be controlled or adjusted by adjusting operation of regulation valve 120 (e.g., adjusting the release rate of gas into chambers 102A, 102B and chamber 104).

After mattress 100 is inflated, the mattress may be moved, along with the attached corpse 108, to a location of a gurney, stretcher, or mortuary cot (e.g., a collapsible, wheeled cot typically used to carry and move a corpse from a remote location to a mortuary). FIG. 8 depicts a representation of an embodiment of corpse 108 on mattress 100, in the inflated state, positioned next to gurney 150.

To move mattress 100 with corpse 108 attached, personnel may grab the mattress using handles 110. Handles 110 are positioned to allow personnel to easily grab and move mattress 100 with corpse 108 on the mattress. Handles 110 on the ends of mattress 100 (e.g., the handles attached to chamber 104) may be positioned higher and easier for the personnel to grab and lift the mattress. Handles 110 on the side of mattress 100 (e.g., the handles attached to chambers 102A, 102B) may be used for additional grabbing and manipulation of the mattress. In some embodiments, handles 110 may include extensions or have extensions attached to the handles. The extensions may allow grabbing of mattress 100 at increased distances from the mattress.

Because mattress 100 is an inflatable structure inflated with gas to provide a firm and stable support for corpse 108, mattress 100 may have a relatively light weight. For example, in certain embodiments, mattress 100 may have a weight of at most about 20 pounds. In some embodiments, mattress 100 may have a weight of at most about 15 pounds or at most about 10 pounds.

With the light weight, mattress 100 provides a stable platform for moving corpse 108 from the location of death to the location of gurney 150. While providing a lightweight and stable platform, mattress 100 may also be moved between locations more easily than other mattresses or corpse support apparatus. The structure of mattress 100 allows the mattress to flex and/or bend while corpse 108 is attached to the mattress. For example, the shape and construction of chambers 102A, 102B and chamber 104 allow mattress 100 to flex and/or bend while inflated. Flexing and/or bending of mattress 100 while moving the mattress allows the mattress to be more easily maneuvered around corners, through doorways, and over or around objects. Additionally, as chambers 102A, 102B include sliding material surfaces 114 (shown in FIG. 4), mattress 100 may be glide or slid over surfaces such as floors, stairs, hallways, or wall corners. The gliding movement of mattress 100 allows personnel to more easily move the mattress between locations, especially for corpses of greater weight that may be more difficult to lift and carry off the floor (e.g., corpses above about 250 pounds).

Figure 9:
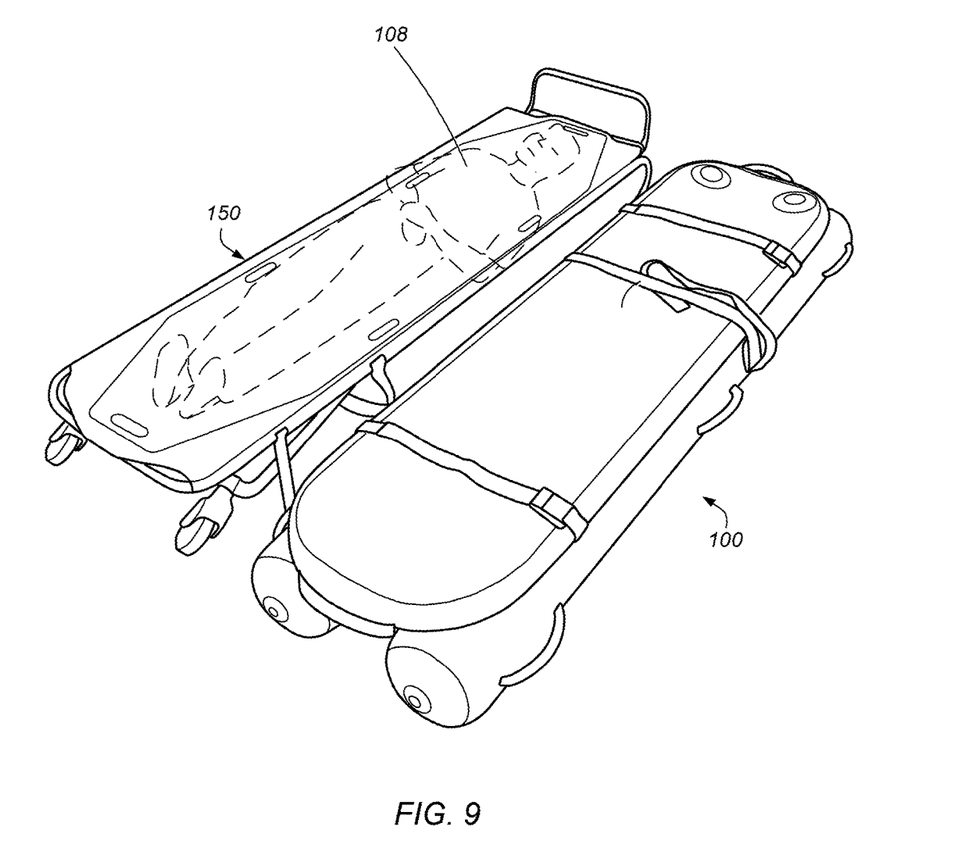
FIG. 9 depicts a representation of an embodiment of a corpse having been moved to a gurney from an inflatable mattress.

After mattress 100 and corpse 108 are moved to the location of gurney 150, as shown in FIG. 8, the corpse may be transferred to the gurney. FIG. 9 depicts a representation of an embodiment of corpse 108 having been moved to gurney 150 from mattress 100. In the inflated state, mattress 100 raises corpse 108 to substantially the same height as the upper surface of gurney 150 (which may be in a collapsed or folded down position). Because the upper surfaces of mattress 100 and gurney 150 are at substantially the same height, transferring of corpse 108 from the mattress to the gurney is relatively easy. In some embodiments, corpse 108 is transferred using a Smooth Mover or other thin board (which may have remained positioned under the corpse on the mattress).

After corpse 108 is transferred to gurney 150, the corpse may be moved (transported) to another location such as a mortuary or coroner's office using the gurney. Mattress 100 may be deflated by releasing gas through pressure valves 124. Mattress may be cleaned as needed and rolled into a rolled-up state and placed in the carry bag, if desired.

It is to be understood the invention is not limited to particular systems described which may, of course, vary. It is also to be understood that the terminology used herein is for the purpose of describing particular embodiments only, and is not intended to be limiting. As used in this specification, the singular forms "a", "an" and "the" include plural referents unless the content clearly indicates otherwise. Thus, for example, reference to "a portion" includes a combination of two or more portions and reference to "a material" includes mixtures of materials.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for lifting and transporting a human body, comprising:
   moving the human body onto an inflatable mattress that is in a deflated state, the inflatable mattress comprising an inflatable mattress chamber in fluid communication with two elongated inflatable chambers positioned lengthwise along longitudinal edges of the inflatable mattress chamber, wherein the two elongated chambers are positioned at least partially underneath the longitudinal edges of the inflatable mattress chamber;
   securing the human body to at least part of a top surface of the inflatable mattress chamber;
   at least partially inflating the inflatable mattress with compressed gas provided into the inflatable mattress chamber and the two elongated inflatable chambers to raise the human body located on the top surface of the inflatable mattress chamber to a selected inflated height, the top surface of the inflatable mattress chamber comprising a firm surface that support the human body after inflation, wherein the two elongated inflatable chambers, when inflated, have an inflated height, and wherein the inflatable mattress comprises a lower planar surface that is raised to the inflated height of the two elongated inflatable chambers when the two elongated inflatable chambers are inflated;
   wherein the lower planar surface of the inflatable mattress chamber is in tangential contact with both of the two elongated inflatable chambers along the outer surfaces of the two elongated inflatable chambers at the inflated height; and
   moving the human body, while the human body is secured to the inflated mattress, from a first location to a second location.

2. The method of claim 1, wherein the human body comprises a human corpse, and wherein the first location comprises a location the human died.

3. The method of claim 2, further comprising moving the inflatable mattress and the coupled human corpse to a location of a mortuary cot while the mattress is inflated.

4. The method of claim 1, further comprising moving the human body onto the mattress at the first location, securing the human body to at least part of the top surface of the mattress chamber at the first location, at least partially inflating the inflatable mattress with compressed gas provided into the inflatable mattress chamber and the two elongated inflatable chambers to raise the human body to the selected inflated height at the first location, and then moving the inflated mattress with the secured human body to the second location.

5. The method of claim 1, further comprising moving the human body onto the inflatable mattress that is in the deflated state by at least partially lifting the human body and sliding the inflatable mattress under at least a portion of the human body.

6. The method of claim 1, further comprising at least partially inflating the inflatable mattress with compressed gas provided from a source attached to the inflatable mattress.

7. The method of claim 1, wherein the two elongated inflatable chambers comprise portions that are at least partially positioned outside the longitudinal edges of the inflatable mattress chamber.

8. The method of claim 1, further comprising inflating the inflatable mattress to the selected height in less than about 90 seconds.

9. The method of claim 1, wherein the inflatable mattress chamber comprises a rectangular mattress chamber.

10. An apparatus for lifting and transporting a human body, comprising:
    an inflatable mattress, the inflatable mattress comprising an inflatable mattress chamber in fluid communication with two elongated inflatable chambers, the two elongated inflatable chambers being positioned lengthwise along longitudinal edges of the inflatable mattress chamber, wherein the two elongated inflatable chambers are positioned at least partially underneath the longitudinal edges of the inflatable mattress chamber, and wherein the inflatable mattress chamber comprises one or more devices for coupling the human body to a top surface of the inflatable mattress chamber, the top surface of the inflatable mattress chamber comprising a firm surface that supports the human body when inflated;
    an inflation device coupled to the inflatable mattress chamber and the two elongated inflatable chambers, the inflation device configured to inflate the inflatable mattress chamber and the two elongated inflatable chambers to raise the inflatable mattress chamber to a selected inflated height with the human body coupled to the inflatable mattress chamber;
    wherein, when inflated, the two elongated inflatable chambers have an inflated height, and wherein a lower planar surface of the inflatable mattress chamber is in tangential contact with both of the two elongated inflatable chambers along their outer surfaces at the inflated height of the two elongated inflatable chambers; and wherein the inflatable mattress is movable, with the human body coupled to the inflatable mattress, from a first location to a second location.

11. The apparatus of claim 10, wherein at least some portion of each of the two elongated inflatable chambers are positioned outside the longitudinal edges of the inflatable mattress chamber.

12. The apparatus of claim 10, wherein at least a portion of each of the two elongated inflatable chambers provide support for the inflatable mattress chamber when inflated.

13. The apparatus of claim 10, wherein a lower surface of the elongated inflatable chambers comprises sliding material that allows the inflatable mattress to be moved across surfaces.

14. The apparatus of claim 10, wherein the devices for coupling the human body to the top surface of the inflatable mattress chamber comprise adjustable straps.

15. The apparatus of claim 10, wherein the inflation device comprises a compressed gas cylinder attached to the inflatable mattress chamber and the two elongated inflatable chambers.

16. The apparatus of claim 15, wherein the compressed gas comprises carbon dioxide.

17. The apparatus of claim 10, wherein the inflation device is positioned in a pouch attached to the inflatable mattress chamber.

18. The apparatus of claim 10, wherein the inflatable mattress chamber comprises a rectangular mattress chamber.

19. The apparatus of claim 10, wherein the lower planar surface of the inflatable mattress chamber is in tangential contact with both of the two elongated inflatable chambers longitudinally along the outer surfaces of the two elongated inflatable chambers at the inflated height.

* * * * *